(12) United States Patent
Powell et al.

(10) Patent No.: US 10,282,518 B2
(45) Date of Patent: May 7, 2019

(54) SYSTEMS AND METHODS FOR VIEWING ELECTROCARDIOGRAMS

(75) Inventors: William Cameron Powell, San Antonio, TX (US); Stephen Trey Moore, San Antonio, TX (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 83 days.

(21) Appl. No.: 13/980,295

(22) PCT Filed: Jan. 18, 2012

(86) PCT No.: PCT/US2012/021677
§ 371 (c)(1),
(2), (4) Date: Sep. 30, 2013

(87) PCT Pub. No.: WO2012/099933
PCT Pub. Date: Jul. 26, 2012

(65) Prior Publication Data
US 2014/0019901 A1   Jan. 16, 2014

Related U.S. Application Data

(60) Provisional application No. 61/433,824, filed on Jan. 18, 2011.

(51) Int. Cl.
*G06F 19/00* (2018.01)
*A61B 5/00* (2006.01)
(Continued)

(52) U.S. Cl.
CPC ............ *G06F 19/34* (2013.01); *A61B 5/0006* (2013.01); *A61B 5/0022* (2013.01); *A61B 5/044* (2013.01);
(Continued)

(58) Field of Classification Search
CPC ............ G06F 19/3406; G06F 3/04842; G06F 3/0482; G06F 3/04847
See application file for complete search history.

(56) References Cited

U.S. PATENT DOCUMENTS 5,072,383 A * 12/1991 Brimm .................. G06F 19/327
705/2
5,410,473 A    4/1995 Kaneko et al.
(Continued)

FOREIGN PATENT DOCUMENTS

EP    1406198    4/2004
JP    9051880 A  2/1997
(Continued)

OTHER PUBLICATIONS

European Search Report for Application No. 12736833.0 dated Jun. 30, 2014 (2 pages).
(Continued)

*Primary Examiner* — Shourjo Dasgupta
(74) *Attorney, Agent, or Firm* — Fish & Richardson P.C.

(57) ABSTRACT

Methods, systems, and apparatus, including computer programs encoded on a computer storage medium, for displaying an electrocardiogram (ECG) on a computing device using actions including receiving data corresponding to the ECG, processing the data to generate a plurality of traces, displaying a plurality of trace display windows, displaying each trace of the plurality of traces in a trace window of the plurality of trace windows, receiving user input corresponding to at least one trace window of the plurality of trace windows, and modifying a display of each trace of the plurality of traces in the respective trace display windows in response to the user input.

18 Claims, 11 Drawing Sheets

(51) Int. Cl.
*A61B 5/044* (2006.01)
*G06F 3/0485* (2013.01)
*G16H 15/00* (2018.01)
*G06F 3/14* (2006.01)
*G09G 5/12* (2006.01)

(52) U.S. Cl.
CPC ........ *G06F 3/0485* (2013.01); *G06F 19/3418* (2013.01); *G16H 15/00* (2018.01); *A61B 5/7475* (2013.01); *G06F 3/1415* (2013.01); *G06F 3/1431* (2013.01); *G06F 2203/04806* (2013.01); *G09G 5/12* (2013.01); *G09G 2380/08* (2013.01)

(56) References Cited

U.S. PATENT DOCUMENTS

| | | | | |
|---|---|---|---|---|
| 5,491,781 | A * | 2/1996 | Gasperina | G06F 3/04855 345/660 |
| 5,581,275 | A | 12/1996 | Glei et al. | |
| 5,739,817 | A | 4/1998 | Glei et al. | |
| 6,006,191 | A * | 12/1999 | DiRienzo | G06F 19/321 705/2 |
| 6,166,736 | A * | 12/2000 | Hugh | G06F 3/0481 715/777 |
| 6,934,578 | B2 * | 8/2005 | Ramseth | A61B 5/044 600/523 |
| 7,844,917 | B2 * | 11/2010 | Rigolet | G06F 3/0481 715/788 |
| 8,464,177 | B2 * | 6/2013 | Ben-Yoseph | G06F 3/0481 715/792 |
| 2003/0117296 | A1 * | 6/2003 | Seely | A61B 5/0002 340/870.07 |
| 2004/0017475 | A1 * | 1/2004 | Akers | G06Q 50/22 348/207.1 |
| 2004/0051721 | A1 * | 3/2004 | Ramseth | G06F 19/3406 345/689 |
| 2004/0054261 | A1 * | 3/2004 | Kamataki | A61B 5/0002 600/300 |
| 2004/0260192 | A1 | 12/2004 | Yamamoto | |
| 2005/0010165 | A1 * | 1/2005 | Hickle | A61B 5/417 604/66 |
| 2007/0250788 | A1 * | 10/2007 | Rigolet | G06F 3/0481 715/788 |
| 2008/0052637 | A1 * | 2/2008 | Ben-Yoseph | G06F 3/0481 715/800 |
| 2009/0054743 | A1 * | 2/2009 | Stewart | G06T 11/206 600/301 |
| 2011/0004071 | A1 * | 1/2011 | Faiola | A61B 5/7445 600/300 |
| 2014/0351738 | A1 * | 11/2014 | Kokovidis | A61B 5/7445 715/771 |
| 2015/0248534 | A1 * | 9/2015 | Krzywicki | G06F 19/3406 715/771 |

FOREIGN PATENT DOCUMENTS

| | | |
|---|---|---|
| JP | 11216119 A | 8/1999 |
| JP | 2004174230 A | 6/2004 |
| WO | WO2010105063 A1 | 9/2010 |

OTHER PUBLICATIONS

European Examination Report for Application No. 12736833.0 dated Jul. 15, 2014 (6 pages).
International Search Report and Written Opinion from corresponding International Application No. PCT/US2012/021677 dated Aug. 31, 2012 (11 pages).
Plaintiffs' Complaint for Patent Infringement, *Airstrip Technologies, Inc. et al.* v. *mVISUM, Inc.*, Civil Action No. 1:12cv-07776-JFK, United States District Court for the Southern District of New York, Document 1, filed Oct. 18, 2012, 30 pages.
Defendant's Answer and Counterclaim, *Airstrip Technologies, Inc. et al.* v. *mVISUM, Inc.*, Civil Action No. 1:12-cv-07776-JFK, United States District Court for the Southern District of New York, Document 29, filed Apr. 5, 2013, 13 pages.
GE Healthcare, "Web Viewer and Pocket Viewer," 2007, retrieved from http://www3.gehealthcare.com/~/media/Downloads/us/Product/Product-Categories/Patient-Monitoring/Careports/Mobile-Viewers/GEHealthcare-Web-Viewer-Pocket-Viewer-ProductSpec.pdf?Parent=%7B1ED25767-3F69-413B-8C56-3DDEA5CEF31F%7D, 4 pages.
Edward H. Schmuhl et al., "HP PalmVue: A New Healthcare Information Product," Hewlett-Parkard Journal, Article 8, Jun. 1996, retrieved from http://www.hpl.hp.com/hpjournal/96jun/jun96a8.pdf, pp. 12-17.
MobileInfo, "Data Critical's StatView™ Alarm Notification System," Jun. 2000, retrieved from http://www.mobileinfo.com/Applications_Vertical/Healthcare_Applications/StatView.htm, 2 pages.
Telecompaper, "Data Critical Launches Rhythmstat XL Medical System," Jan. 8, 1998, retrieved from http://www.telecompaper.com/news/data-critical-launches-rhythmstat-xl-medical-system--26725, 2 pages.
U.S. Food and Drug Administration, Protecting and Promoting Your Health, "MAUDE Adverse Event Report: Data Critical Corp. Impactpaging System," Nov. 19, 2000, retrieved on Apr. 8, 2013 from <www.accessdata.fda.gov/scripts/cdrh/cfdocs/cfmaude/detail.cfm?mdrfoi_id=312735>, 2 pages.
Department of Health & Human Services, Food and Drug Administration, Center for Devices and Radiological Health, 510(k) Summary and approval letter for FlexView™ Clinical Monitoring System (K003998), Mar. 7, 2001, 4 pages.
Department of Health & Human Services, Food and Drug Administration, Center for Devices and Radiological Health, 510(k) Summary and approval letter for AlarmView™ Wireless Data Network System (K010912), Apr. 5, 2001, 4 pages.
Department of Health & Human Services, Food and Drug Administration, Center for Devices and Radiological Health, 510(k) Summary and approval letter for Agilent Information Center (AIC) Software Release D.0 (K011093), May 1, 2001, 5 pages.
Department of Health & Human Services, Food and Drug Administration, Center for Devices and Radiological Health, 510(k) Summary and approval letter for Mobile-PatientViewer™ (K011436), Jul. 5, 2001, 5 pages.
Department of Health & Human Services, Food and Drug Administration, Center for Devices and Radiological Health, 510(k) Summary and approval letter for FlexView™ Clinical Monitoring System (K011999), Jul. 24, 2001, 4 pages.
Department of Health & Human Services, Food and Drug Administration, Center for Devices and Radiological Health, 510(k) Summary and approval letter for AlarmView™ Wireless Data Network System (K012005), Jul. 24, 2001, 4 pages.
Department of Health & Human Services, Food and Drug Administration, Center for Devices and Radiological Health, 510(k) Summary and approval letter for AlarmView™ Wireless Data Network System (K013156), Oct. 19, 2001, 4 pages.
Department of Health & Human Services, Food and Drug Administration, Center for Devices and Radiological Health, 510(k) Summary and approval letter for Datex-Ohmeda S/5 Web Viewer, Datex-Ohmeda S/5 Pocket Viewer and Datex-Ohmeda S/5 Cellular Viewer with L-WEB04 software (K052975), Jan. 20, 2006, 7 pages.
Department of Health & Human Services, Food and Drug Administration, Center for Devices and Radiological Health, 510(k) Summary and approval letter for Web Viewer, Pocket Viewer and Cellular Viewer with L-WEB05 software (K061994), Aug. 11, 2006, 4 pages.
Department of Health & Human Services, Food and Drug Administration, Center for Devices and Radiological Health, 510(k) Summary and approval letter for RhythmStat XL System (K971650), Dec. 4, 1997, 9 pages.
Department of Health & Human Services, Food and Drug Administration, Center for Devices and Radiological Health, 510(k) Summary and approval letter for Cardio-Pager™ System (K973527), Mar. 31, 1998, 6 pages.
Department of Health & Human Services, Food and Drug Administration, Center for Devices and Radiological Health, 510(k) Sum-

(56) References Cited

OTHER PUBLICATIONS mary and approval letter for Hewlett-Packard M2605A Viridia Wave Viewer (K974567), Jan. 20, 1998, 5 pages.
Department of Health & Human Services, Food and Drug Administration, Center for Devices and Radiological Health, 510(k) Summary and approval letter for StatView™ System (K990378), Sep. 20, 1999, 6 pages.
Department of Health & Human Services, Food and Drug Administration, Center for Devices and Radiological Health, 510(k) Summary and approval letter for AlarmView™ System (K992848), Nov. 19, 1999, 6 pages.
International Preliminary Report on Patentability from corresponding International Application No. PCT/US2012/021677 dated Aug. 1, 2013 (8 pages).
Patent Examination Report No. 1 for Australian Patent Application No. 2012207410 dated Aug. 21, 2015 (2 pages).
Patent Examination Report for Chinese Patent Application No. 201280014044.9 dated Jul. 23, 2015 (16 pages).
Patent Examination Report No. 1 for Australian Patent Application No. 2012207410 dated Jan. 29, 2016 (3 pages).
Patent Examination Report for Chinese Patent Application No. 201280014044.9 dated Mar. 23, 2016 (25 pages).
Daoming Zhang, "The System of Analysis and Auxiliary Diagnosis of Electrocardiogram," China Doctoral Dissertations, Science-Engineering (B), vol. 2010, No. 3, Mar. 15, 2010, pp. C030-C035.
Wei Meng, "Design of Portable Sleep Monitor Based on Pulse Transiting Time," Chinese Master's Theses, Science-Engineering (B), vol. 2010, vol. 8, Aug. 15, 2010, pp. C030-C049.
Notice of Reasons for Rejection for Japanese Patent Application No. 2013-550551, dated Dec. 2, 2015 (6 pages).
Patent Examination Report for Chinese Patent Application No. 201280014044.9 dated Oct. 17, 2016 (10 pages).
Decision of Rejection for Japanese Patent Application No. 2013-550551, dated Aug. 18, 2016 (4 pages).
Authorized Officer Clara Neppel, European Summons to Attend Oral Proceedings Pursuant to Rule 115(1) EPC for Application No. 12736833.0 dated Nov. 17, 2016 (5 pages).
Patent Examination Report (English translation) for Chinese Patent Application No. 201280014044.9 dated Oct. 17, 2016 (21 pages).
Rejection Decision (English translation) for Chinese Patent Application No. 201280014044.9 dated Mar. 2, 2017 (21 pages).
Examination Report for Canadian Patent Application No. 2825195 dated Aug. 22, 2017 (7 pages).
Patent Examination Report (including English translation) for Chinese Patent Application No. 201280014044.9 dated Aug. 17, 2017 (4 pages).
Authorized Officer Clara Neppel, European Brief Communication for Application No. 12736833.0 dated Feb. 17, 2017 (5 pages).
Authorized Officer Clara Neppel, European Result of Consultation for Application No. 12736833.0 dated Feb. 28, 2017 (6 pages).
Examination Report for Canadian Patent Application No. 2825195 dated Aug. 7, 2018 (3 pages).

* cited by examiner

SYSTEMS AND METHODS FOR VIEWING ELECTROCARDIOGRAMS

CROSS-REFERENCE TO RELATED APPLICATION

This application is a National Stage application under 35 U.S.C. § 371 of International Application No. PCT/US2012/021677, having an International Filing Date of Jan. 18, 2012, which claims the benefit of U.S. Provisional Application No. 61/433,824, filed Jan. 18, 2011. The disclosure of the foregoing application is hereby incorporated by reference in its entirety.

FIELD

This invention generally relates to systems and methods for transmitting, receiving and displaying data and/or information over wireless communication and data processing devices, and more specifically to a system and method for collecting, uploading, transmitting, receiving, downloading, manipulating, and displaying medical patient data and/or information to a remote device operable by a health care provider.

SUMMARY

In some aspects, the present disclosure provides display of electrocardiograms (ECGs). In some aspects, methods for displaying an ECG on a computing device include receiving data corresponding to the ECG, processing the data to generate a plurality of traces, displaying a plurality of trace display windows, displaying each trace of the plurality of traces in a trace window of the plurality of trace windows, receiving user input corresponding to at least one trace window of the plurality of trace windows, and modifying a display of each trace of the plurality of traces in the respective trace display windows in response to the user input.

In some aspects, the user input indicates a zoom event, and modifying includes zooming each trace within a respective trace display window.

In some aspects, the user input indicates a scroll event, and modifying includes scrolling each trace within a respective trace display window.

In some aspects, modifying the display of each trace comprises simultaneous and time synchronized modification of each trace.

In some aspects, methods further include processing the data to generate a plurality of full traces, displaying a plurality of full trace display windows, and displaying each full trace of the plurality of full traces in a full trace window of the plurality of full trace windows. In some aspects, the full traces displayed in the plurality of full trace display windows remain unmodified in response to the user input.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

The present disclosure provides a healthcare provider with secure, remote access to patient data. For purposes of the instant description, and by way of non-limiting example, implementations of the present disclosure will be described in the context of patient data corresponding to electrocardiograms (ECGs).

Figure 1:
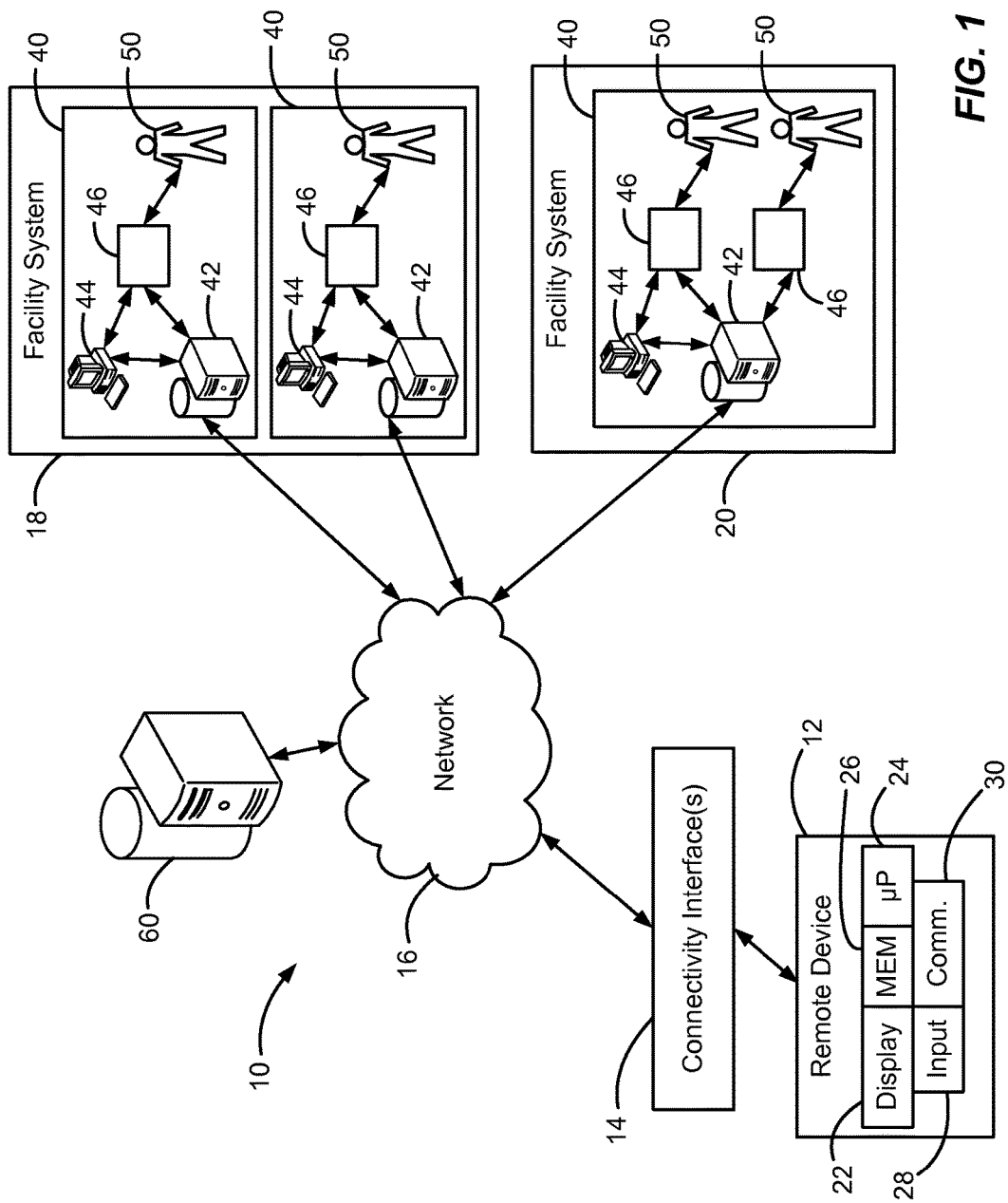
FIG. 1 is a schematic illustration of an example system architecture in accordance with the present disclosure.

Referring now to FIG. 1, an example system architecture 10 is illustrated, and includes a remote device 12, connectivity interface(s) 14, a network 16, a first facility system 18, and a second facility system 20. As discussed in further detail herein, data is transferred from each of the first and second facility systems 18, 20 through the network 16 and connectivity interface(s) 14 for presentation, or display on the remote device 12. Further, data can be transferred from the remote device 12 through the connectivity interface(s) 14 and network 16 to each of the first and second facility systems 18, 20. Although a single remote device 12 is illustrated, it is contemplated that one or more remote devices 12 can communicate with each of the first and second facility systems 18, 20 through the network 16 and connectivity interface(s) 14. Similarly, although two facility systems are illustrated, the present disclosure can be implemented with one or more facility systems.

The remote device 12 can include any number of devices. Such devices include, but are not limited to, a mobile phone, a smartphone, a personal digital assistant (PDA), a laptop, a tablet personal computer (PC), a desktop PC, a set-top box, an interactive television and/or combinations thereof. The remote device 12 includes a display 22, a processor 24, memory 26, an input interface 28, and a communication interface 30. The processor 24 can process instructions for execution of implementations of the present disclosure. The instructions can include, but are not limited to, instructions stored in the memory 26 to display graphical information on the display 22. Displays include, but are not limited to, a thin-film-transistor (TFT) liquid crystal display (LCD), or an organic light emitting diode (OLED) display.

The memory 26 stores information within the remote device 12. In some implementations, the memory 26 can include a volatile memory unit or units, and/or a non-volatile memory unit or units. In other implementations, removable memory can be provided, and can include, but is not limited to, a memory card. Exemplar memory cards can include, but are not limited to, a secure digital (SD) memory card, a mini-SD memory card, a USB stick, and the like.

The input interface 28 can include, but is not limited to, a keyboard, a touchscreen, a mouse, a trackball, a microphone, a touchpad, and/or combinations thereof. In some implementations, an audio codec (not shown) can be provided, which receives audible input from a user or other source through a microphone, and converts the audible input to usable digital information. The audio codec can generate audible sound, such as through a speaker that is provided with the remote device 12. Such sound may include, but is not limited to, sound from voice telephone calls, recorded sound (e.g., voice messages, music files, etc.), and sound generated by applications operating on the remote device 12.

The remote device 12 may communicate wirelessly through the communication interface(s) 14, which can include digital signal processing circuitry. The communication interface(s) 14 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the remote device can be capable of short-range communication using features including, but not limited to, Bluetooth and/or WiFi transceivers (not shown).

The remote device 12 communicates with the network 16 through the connectivity interface(s) 14. The connectivity interface(s) 14 can include, but is not limited to, a satellite receiver, cellular network, a Bluetooth system, a Wi-Fi system (e.g., 802.x), a cable modem, a DSL/dial-up interface, and/or a private branch exchange (PBX) system. Each of these connectivity interfaces 14 enables data to be transmitted to/from the network 16. The network 16 can be provided as a local area network (LAN), a wide area network (WAN), a wireless LAN (WLAN), a metropolitan area network (MAN), a personal area network (PAN), the Internet, and/or combinations thereof.

In the systems of FIG. 1, the first facility system 18 includes a plurality of facilities 40, and the second facility system 20 includes a facility 40. It is contemplated that each facility system 18, 20 can include one or more facilities, and is not limited to the exemplar arrangement described herein. In the case of multiple facilities, the facilities can be remotely located from one another, and/or can be located at a common location, or site (e.g., separate departments in a common building). Each facility system 18, 20 can be provided as a medical care system, for example, which medical care system can include one or more hospitals, hospital systems, clinics, physician offices, and the like.

Each facility 40 includes an associated patient information system 42, computer interface(s) 44, and patient monitoring device(s) 46. In some implementations, the patient information system 42 can be provided as, or can include a cardiology information system. Each patient information system 42 can be provided as a server, and supports the acquisition, storage, modification, and distribution of clinical information, such as patient data, throughout the facility 40 and/or facility system 18, 20. Each patient information system 42 can communicate with one or more ancillary information systems (not shown) that can include, but are not limited to, a pharmacy management system, a laboratory management system, and/or a radiology management system. Although the system architecture 10 includes a patient information system 42 located at each facility 40, it is contemplated that the facilities 40 can communicate with a common patient information system 42 that is remotely located from either facility 40, or that is located at one of the facilities 40 within the facility system 18, 20.

The computer interface 44 can communicate with the patient information system 42 to enable access to information that is stored within, and managed by the patient information system 42. The computer interface 44 can include, but is not limited to, a personal computer (PC) (e.g., desktop, laptop, or tablet). Although a single computer interface 44 is illustrated in the exemplar architectures described herein, it is contemplated that one or more computer interfaces 44 can communicate with the patient information system 42. Communication between each computer interface 44 and the patient information system 42 can be achieved via a direct connection, or remotely through a network (not shown) that can include, but is not limited to, a LAN, a WAN, a WLAN, and/or the Internet.

Each patient monitoring device 46 monitors physiological characteristics of a particular patient 50, and generates data signals based thereon. In the example context of the present disclosure, the patient monitoring devices 46 include ECG recording devices. The data signals are communicated to the patient information system 42 and/or the computer interface 44, each of which can collect patient data based thereon, and store the data to a patient profile that is associated with the particular patient. The patient monitoring device 46 can communicate with the patient information system 42 and/or the computer interface 44 via a direct connection, or remotely through a network (not shown) that can include, but is not limited to, a LAN, a WAN, a WLAN, and/or the Internet.

A health care professional, such as a doctor, a nurse and/or a technician, can generate one or more ECGs for a particular patient using an ECG recording device. In general, electrodes are attached to various locations on the anatomy of the particular patient and each electrode is in electrical communication with the ECG recording device. By way of non-limiting example, an example ECG recording device can include a 12-lead ECG recording device having 10 electrodes that communicate with the ECG recording device through electrical cables or wires. It is appreciated, however, that implementations of the present disclosure are applicable to ECGs generated using any type of ECG recording device. With reference to the example 12-lead ECG recording device, the electrodes can include a right arm (RA) electrode, a left arm (LA) electrode, a right leg (RL) electrode, a left leg (LL) electrode, and torso electrodes ($V_1$-$V_6$).

In some implementations, the term lead refers to the resultant traces of the voltage difference between two of the electrodes, which traces make up the resulting ECG. For example, lead I (I) is provided as the voltage difference between the RA electrode and the LA electrode, lead II (II) is provided as the voltage difference between the LL electrode and the RA electrode, and lead III (III) is provided as the difference between the LL electrode and the LA electrode. Augmented vector leads (e.g., aVR, aVL and aVF) are provided based on the voltages provided by the RA, LA and LL electrodes and/or the leads I, II and II. Other leads include simple voltage traces provided by the torso electrodes $V_1$-$V_6$. Consequently, a total of 12 leads (I, II, III, aVR, aVL, aVF and $V_1$-$V_6$) can be provided using 10 electrodes. The resultant ECG displays short segments of each of the leads. In the example case of a 12-lead ECG, and as discussed in further detail below, the ECG can be arranged in a grid of 4 columns by 3 rows, the first column including the leads I, II and III, the second column including the leads aVR, aVL and aVF, and the last two columns including the leads $V_1$-$V_6$.

In the case of an ECG recording, the voltage signals generated by the electrodes are provided as patient data. The patient data can be made available for display on the computer interface 44 and/or directly at the patient monitoring device 46. A healthcare provider (e.g., a technician, a nurse and/or physician) can augment the patient data by inputting patient information that is can be stored to a patient information system. More specifically, the healthcare provider can input patient information corresponding to a particular patient 50, which patient information can be stored to the patient profile. By way of one non-limiting example, a nurse can input nursing notes, which nursing notes can be stored to the patient profile in the information system. As used herein, the term patient information includes any information corresponding to a patient that is input and stored to the patient information system 42 through the computer interface 44.

As discussed above, each patient information system 42 stores patient data that can be collected from the patient monitoring devices 46, as well as additional patient information, that can include information that is input by a healthcare provider. The patient information system 42 communicates the patient data and/or the additional patient data to a data management system (DMS) 60. The DMS 60 can be provided as a server, or a virtual server, that runs server software components, and can include data storage including, but not limited to, a database and/or flat files. In the exemplar system architecture of FIG. 1, a common DMS 60 is provided. The common DMS 60 is common to various facility systems 18, 20, and is not associated with a particular facility system 18, 20. Each patient information system 42 communicates with the DMS 60 via a direct connection, or remotely through a network (not shown) that can include, but is not limited to, a LAN, a WAN, a WLAN, and/or the Internet. In the exemplar arrangement of FIG. 1, the DMS 60 communicates with each of the patient information systems 42 through the network 16. The patient information systems 42 communicate patient data and/or patient information to the DMS 60, and the DMS 60 can communicate ancillary information to the patient information system 42. In some implementations, each facility system 18, 20 can include a corresponding DMS 60. In such an arrangement, each patient information system 42 communicates patient data, and/or additional patient data to the DMS 60. Furthermore, and as discussed in further detail below, the DMS 60 can communicate ancillary information to the patient information system 42. Communication between the DMS 60 and the patient information system(s) 42 can be achieved via a direct connection, or remotely through a network (not shown) that can include, but is not limited to, a LAN, a WAN, a WLAN, and/or the Internet.

The example system architecture of FIG. 1, provides for the remote location of data collection at the DMS 60. In such implementations, the DMS 60 can be provided at a third-party site, remote from any of the facilities 40, or facility systems 18, 20. The third-party functions as a DMS host, and the server components are installed on the remotely hosted DMS 60. In some implementations, a business-to-business (B2B) virtual private network (VPN) can be created between the remotely hosted DMS 60 and the network of the facility 40 or facility system 18, 20. In this manner, the facility 40 and/or facility system 18, 20 forgoes the purchase and/or maintenance of another physical server, or DMS 60. Further, the up-time and the status of availability of the DMS 60 are easier to manage on the part of a dedicated third-party. The DMS' access to the network can be attended to by the third-party, as opposed to burdening the facility 40, or the facility systems 18, 20. Further, the third-party can implement virtual server technologies to leverage multiple DMS installations on a single physical server. In such implementations, a plurality of virtual servers are logically partitioned in a single physical server, and each virtual server has the capability of running its own operating system and server components, and can be independently booted.

The DMS 60 synchronizes and transfers data between the remote device 12, or multiple remote devices 12, and multiple cardiology information systems 42. More specifically, the DMS 60 processes and prepares the patient data and/or patient information for transfer to and presentation on the remote device 12, or multiple remote devices 12, from the patient information system 42. The DMS 60 also processes and prepares ancillary information for transfer to and storage in the patient information system 42 from the remote device 12, or multiple remote devices 12 for potential presentation at a corresponding computer interdace 44. An example DMS can include, but are not limited to, the AirStrip Server provided by AirStrip Technologies, LLC, which AirStrip Server includes AirStrip Server Components installed therein.

Figure 2:
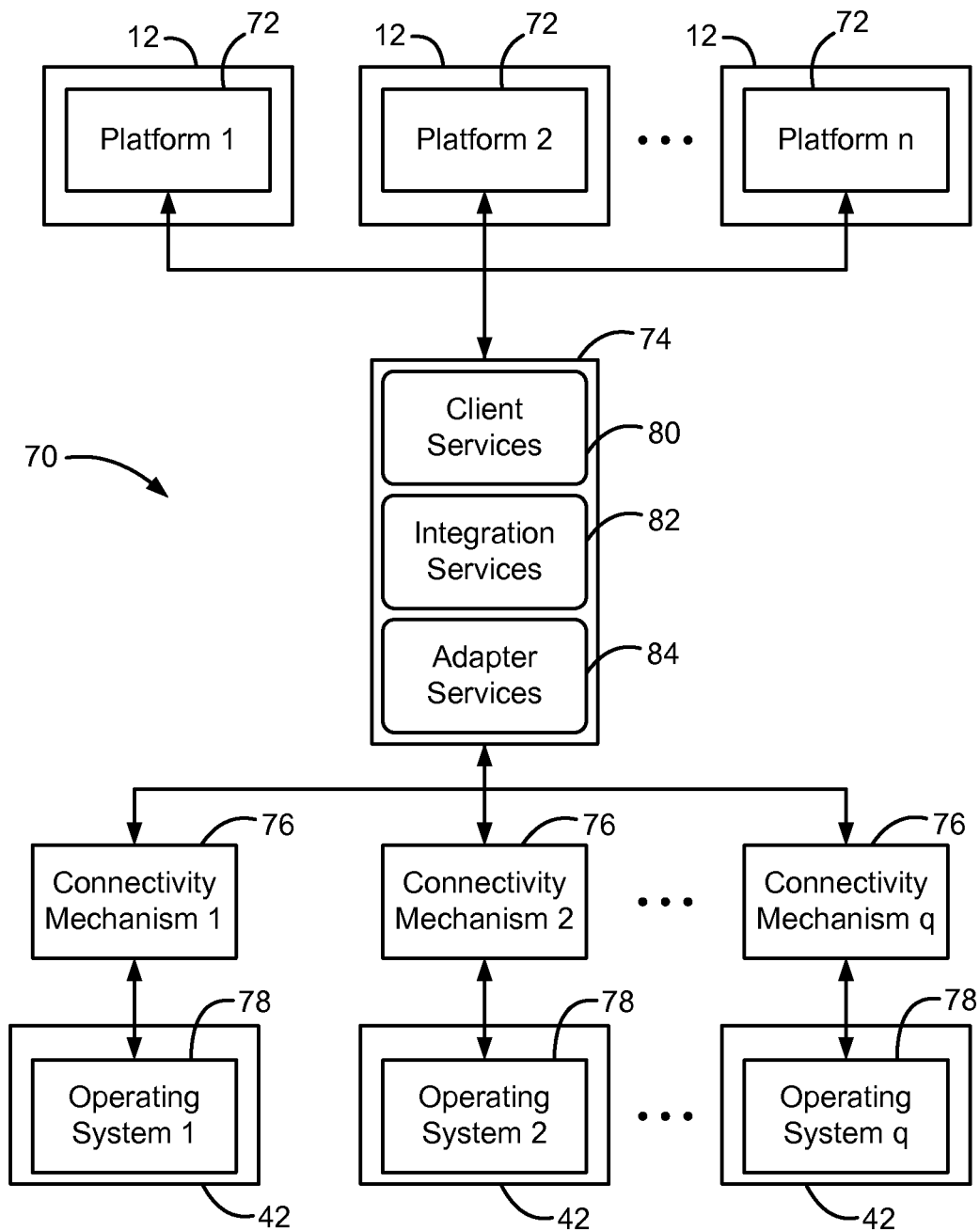
FIG. 2 is a functional block diagram of components that can be used to implement the present disclosure.

Referring now to FIG. 2, a software component, or module structure 70 to implement the features of the present disclosure will be described in detail. The structure enables patient data and patient information to be communicated to/from, and to be synchronized between the patient information system 42 and the remote device 12, regardless of the operating system, or platform, operating on the remote device 12. Platforms include, but are not limited to, RIM Blackberry, Apple iPhone, MS Pocket PC 2003, Win Mobile 5.x (Pocket PC, Smartphone), Win Mobile 6.x (standard, professional), Win Mobile 7.x, Google Android, Palm PRE and/or any platforms to be developed.

FIG. 2 illustrates an overview of the module structure 70, which includes a platform 72, or operating system, of the remote device 12, intermediary components 74, a connectivity mechanism 76, and an operating system 78 of the cardiology information system 42. In this arrangement, the remote device 12 is a client that executes a client application thereon. The intermediary components 74 are resident on the DMS 60, and include a client services module 80, an integration services module 82, and an adapter services module 84. The DMS 60 functions as an intermediary between the platform 72 resident on the remote device 12 and the operating system 78 of the patient information system 42. A plurality of platforms 72 are illustrated to exemplify the ability of the DMS 60 to transfer data to and from any platform 72 operating on the remote device 12. The connectivity mechanism 76 enables communication between the DMS 60 and a particular patient information system 42. A plurality of connectivity mechanisms 76 and corresponding operating systems 78 are illustrated to exemplify the ability of the DMS 60 to transfer data to and from any operating system 78 on the patient information system 42.

Figure 3:
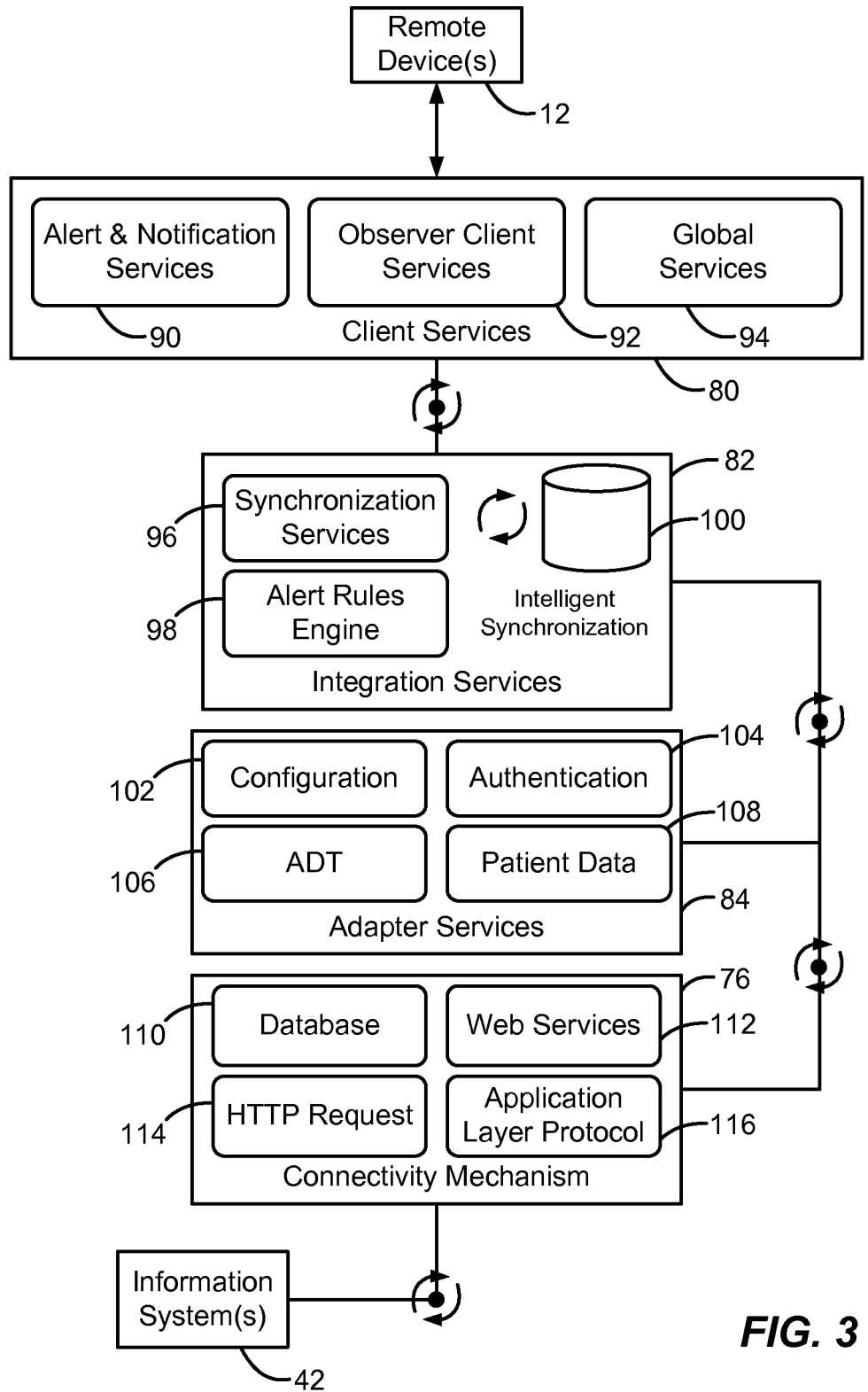
FIG. 3 is a more detailed view of the functional block diagram of FIG. 2.

FIG. 3 depicts detail of the components of FIG. 2. The client services module 80 includes an alert and notification services module 90, an observer client services module 92, and a global services module 94. The integration services module 82 includes a synchronization services module 96, and an alert engines rule 98. The synchronization services module 96 can communicate with a synchronization database 100 to provide so-called intelligent synchronization. The adapter services module 84 includes a configuration module 102, an authentication module 104, an admission, discharge and transfer (ADT) module 106, and a patient data module 108.

The alert and notification services module 90 sends alerts and/or notifications to the remote device 12, as discussed in further detail below. The observer client services module 92 facilitates communication between client applications, running on the remote device 12, and backend server components that provide access to application data. The observer client services module 92 transmits data through a formatted request, and receives data in a proprietary data format. An exemplar data format includes, but is not limited to, JavaScript Object Notation (JSON), which is a lightweight computer data interchange format that provides a text-based, human-readable format for representing simple data structures and associative arrays, called objects). The global services module 94 communicates with the client running on the remote device 12 and performs registration and client application configuration settings. Client application settings can be customized by the user of the remote device 12, and the facility 40 and/or facility systems 18, 20, for which the remote device 12 is configured to receive data.

The integration services module 82 is responsible for routing requests that are received from the observer client services module 92 to retrieve and package requested data, and to send a corresponding response. More specifically, the integration services module 82 requests data from the adapter services module 84, or from the synchronization database 100 depending on how the particular DMS 60 is configured. If the DMS 60 is configured to use a vendor adapter, the request goes directly to the adapter services module 84 to retrieve the data. If the DMS 60 is configured for synchronization, then the data is retrieved from the synchronization database 100. The synchronization services module 96 communicates with the adapter services module 84 to maintain the synchronization database 100 current using intelligent synchronization.

Intelligent synchronization is synchronization executed based on variable configuration parameters, which enable the possibility of only some of the patient data and/or patient information to be synchronized as opposed to all of the available data being continuously synchronized. By using custom business rule logic to intelligently determine which patient data and/or information should be synchronized, and which patient data and/or information should be synchronized, the DMS 60 functions more efficiently and can service an increased number of clients and configurations. By way of non-limiting example, prior to a user logging on to the DMS 60 via the remote device 12, no specific patient data and/or information is synchronized. Instead, only a patient census list and specific data elements corresponding to particular patients 50 are synchronized between the DMS 60 and the patient information system(s) 42. Once the user logs on, and selects a particular patient 50 to review, the synchronization services begin synching all of the available patient data and/or information for that particular patient 50. Consequently, subsequent reviews of the particular patient 50 are much faster, because the patient data and/or information has been synchronized.

The adapter services module 84 is the mechanism that retrieves data from the patient information system 42, through the connectivity mechanism module 76, and that structures the data for the DMS 60. The data is formatted and rules are applied for the specific DMS 60, for which the adapter has been written, regardless of whether the data is directly requested for a client through the integration services module 82, or is retrieved through the synchronization services module 96. The configuration module 102 captures configuration settings used by the patient information system(s) 42. The configuration module 102 can use already existing configuration information so that it does not have to be replicated in the DMS 60. By way of non-limiting example, all of the patient beds of a particular facility 40, and to which unit(s) they belong are typically stored in the patient information system(s) 42. The configuration module 102 reduces, or obviates manual effort in entering the configuration information. The configuration module 102 can also prevent problems from occurring when a configuration change is made in the patient information system(s) 42, but a system administrator forgets to make the change in the DMS 60.

The authentication module 104 handles the authentication needs of the DMS 60, which can include, but are not limited to active directory authentication, vendor authentication, device ID restrictions, device phone number restrictions, and any combination thereof. Each facility system 18, 20 and/or facility 40 is configured to authenticate using any combination of such authentication mechanisms. Device ID restriction is the ability for an authentication service to look at a pre-configured list of device ID's, associated with respective remote devices 12, that are authorized to connect to the facility system 18, 20 and/or facility 40, and only authorizes call from software client that originate with that device ID (i.e., from the particular remote device 12). The device phone number restriction restricts access to remote devices 12 that have a phone number that has been pre-configured in the authentication system.

The ADT module 106 enables the use of existing ADT interfaces within the facility system 18, 20 and/or facility 40 to obtain patient admission, discharge and transfer information in order to always know which patient is associated to which bed and/or unit. The patient data module 108 provides all waveform and non-waveform patient data and/or information from the patient information system(s) 42 to the DMS 60. The patient data module 108 can also provide all waveform and non-waveform acquired from a data acquisition system such as the AirStrip data collector or an independent data collecting system including but not limited to Capsule Technologies' Data Captor system. This includes, but is not limited to, all nursing charting information as well as any automated means of data collection used by the patient information system(s) 42.

In the example structure illustrated in FIG. 3, each connectivity mechanism module 76 includes a database module 110, a web services module 112, a request module 114, and an application layer protocol module 116. By way of non-limiting example, the request module 114 can manage HTTP requests, and/or the application layer protocol can include the health level seven (HL7) application layer protocol. The connectivity mechanism module 76 enables the DMS 60 to connect to and communicate with the particular patient information system 42. In some implementations, the connectivity mechanism module 76 can include application protocol interfaces (APIs), through which it communicates with the patient information system 42. In other implementations, the connectivity mechanism module 76 can directly access the patient information system 42.

Implementations of the present disclosure provide for the graphical representation of one or more ECGs on a remote device. For example, and with reference to FIG. 1, patient data can be provided from one or more patient information systems 42 to a remote device 12 through a DMS 60. The patient data can be processed by one or more applications executed on the remote device to generate a graphical representation of an ECG on a display of the remote device. An example application can include AirStrip Cardiology provided by AirStrip Technologies, LLC.

Figure 4:
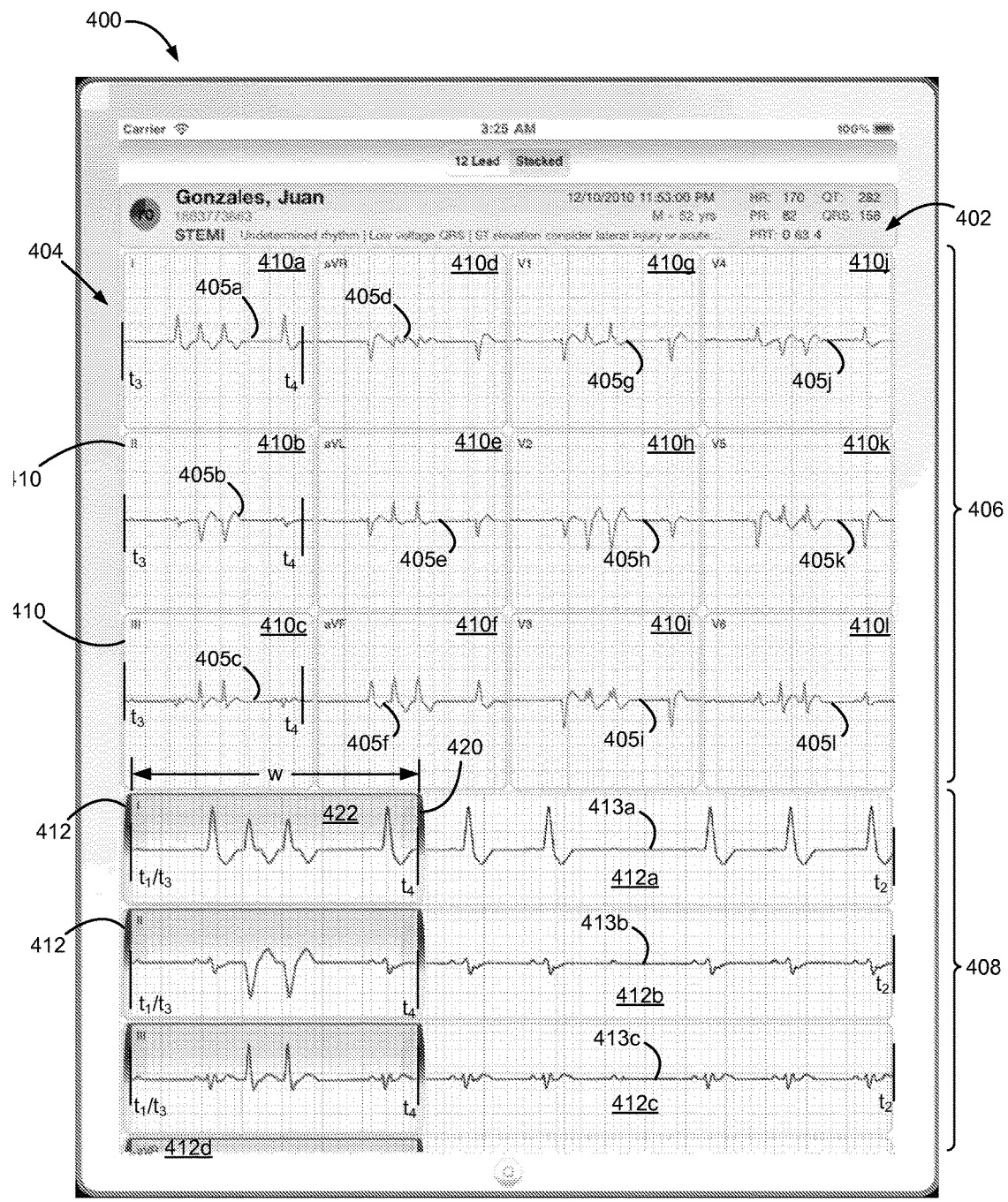
FIGS. 4-10 illustrate a graphical user interface of a remote device in accordance with implementations of the present disclosure.

FIG. 4 illustrates an example graphical user interface (GUI) 400 to graphically represent an ECG on the display of a remote device. The example ECG discussed herein corresponds to a 12-lead ECG. As noted above, implementations of the present disclosure are applicable to any type of ECG. The GUI 400 provides graphical information relating to the data collected from patient monitoring device 46 through cardiology information system 42. In particular, GUI provides cardiology information relating to data collected from electrocardiogram monitors coupled to patients 50.

The GUI 400 includes a patient information area 402 and an ECG area 404. Patient information area 402 includes information such as a name and age of the particular patient, to which the ECG corresponds, the current date and time, and other information (e.g., heart rate, PR interval, QT interval, QRS duration). The ECG area 404 includes a first display area 406, and a second display area 408. The first display area 406 displays a grid of trace windows 410 in 4 columns by 3 rows, the first column including the leads I, II and III, the second column including the leads aVR, aVL and aVF, and the last two columns including the leads $V_1$-$V_6$. Each trace window 410a-410l of the grid includes a respective voltage trace 405a-405l corresponding to the respective lead over a period of time. The trace windows 410a-410l can be used to zoom in and out of and to scroll along segments of the respective voltage traces 405a-405l.

The second display portion 408 includes trace windows 412, each trace window 412 corresponding to a trace window 410 of the first display portion. Consequently, the second display portion 408 can include trace windows 412a-412l having voltage traces 413a-413l, each voltage trace 413a-413l corresponding to a 405a-405l. The voltage traces 413a-413l are each provided as full traces for a particular period of time, graphically representing the data collected over the particular period of time. The trace windows 412 are scrollable, such that un-displayed trace windows (e.g., trace windows 412e-412f), or partially displayed trace windows (e.g., trace window 412d) can be scrolled into full view, while displayed trace windows (e.g., trace windows 412a-412c) can be scrolled from view. The trace windows 412a-412l display the voltage traces 405 for a first time period defined between time $t_1$ and time $t_2$. The trace windows 410a-410l display segments of voltage traces 405a-405l, the segments being over a second time period defined between time $t_3$ and time $t_4$. The second time period falls within the first time period, and is a subset of the first time period.

In accordance with implementations of the present disclosure, a user defines a desired second time period by zooming in/out of and scrolling along one of the voltage traces 405a-405l to display a desired segment of the voltage traces 405a-405l within the trace windows 410a-410l. Accordingly, the trace display windows 410a-410l respectively display segments of the voltage traces 405a-405l, the segments corresponding to respective segments of the voltage traces 413a-413l displayed in the trace display windows 412a-412l. That is, each trace display window 410a-410l can display a full trace or zoomed-in voltage trace 405a-405l corresponding to a voltage trace 413a-413l. As shown in the example of FIG. 4, voltage traces 405a-405l are displayed such that time $t_3$ is substantially the same as time $t_1$ and time $t_4$ is between time $t_1$ and time $t_2$. Consequently, the voltage traces 405a-405l are zoomed-in traces with respect to voltage traces 413a-413l. The voltage traces 405a-405l are synchronized with each other, such that scrolling and/or zooming of a voltage trace 405a-405l in one trace display window 410a-410l results in an equivalent scrolling and/or zooming in each of the other trace display windows 410a-410l. Consequently, each trace display window 410a-410l displays its respective voltage trace 405a-405l for the same second time period defined between time $t_3$ and time $t_4$, in the example of FIG. 4.

With continued reference to FIG. 4, a beveled scrubber bar 420 can be provided in each of the trace windows 412a-412l. The beveled scrubber bar 420 provides a viewing area 422 having a width w. The viewing area 422 displays a portion of the voltage trace 413a-413l corresponding to the portion of the voltage trace 405a-405l displayed in trace display windows 410a-410l. Accordingly, the width w generally corresponds to the time period of the voltage traces 405a-405l. In the example of FIG. 4, the width w correspond to the time period between time $t_3$ and $t_4$. The beveled scrubber bars 420 provide a graphical indicator that enables a user to quickly discern which portion of the voltage traces 413a-413l correspond to the voltage traces 405a-405l.

Figure 5:
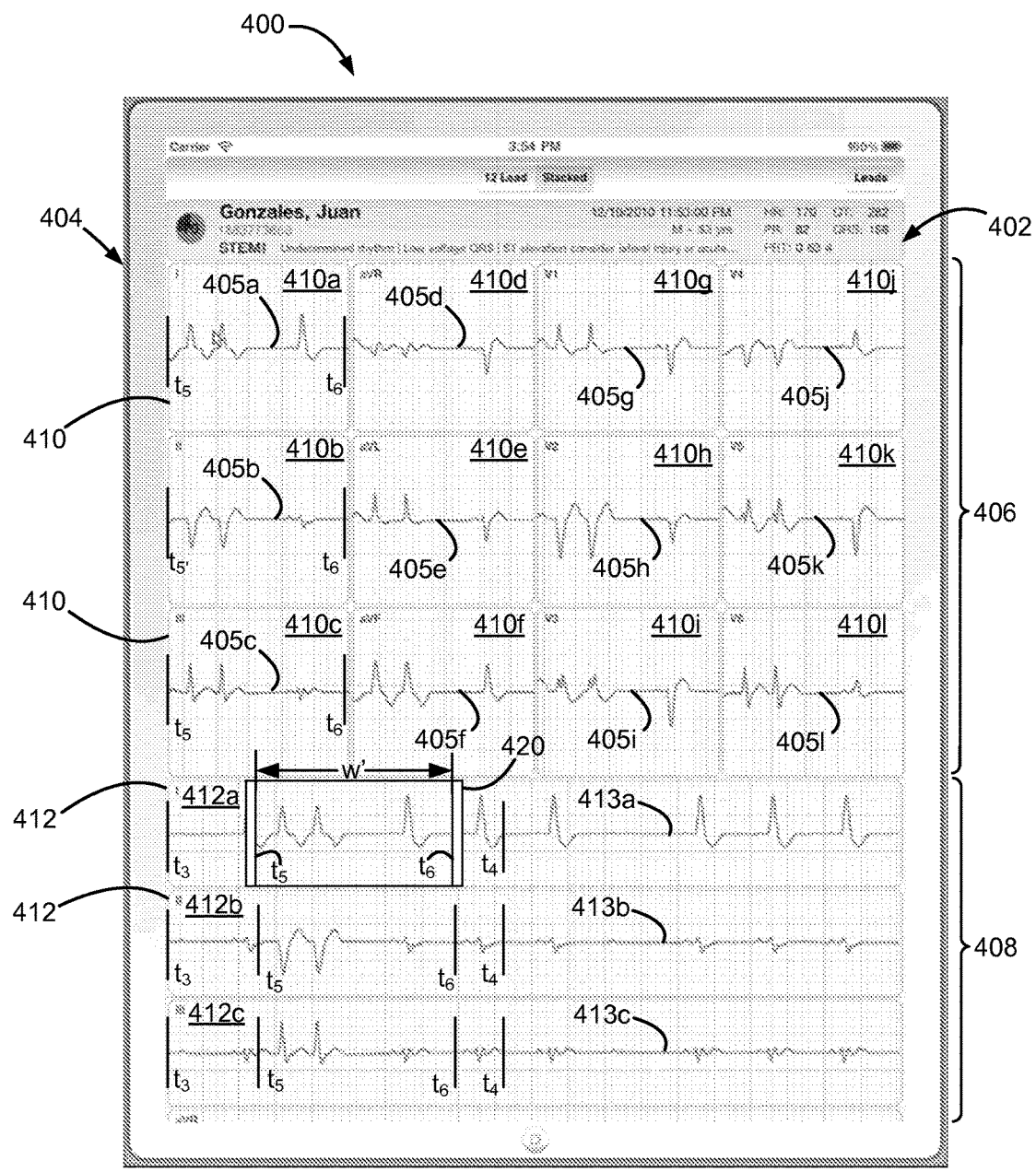

Referring now to FIG. 5, the second time period may be changed (e.g., by scrolling and/or zooming within at least one of the trace display windows 410a-410l) to display different segments of the voltage traces 405a-405l. For example, a user can provide input (e.g., touchscreen input) associated with trace display window 410a to zoom in on the voltage trace 405a, providing the zoomed in segment of voltage trace 405a of FIG. 5, relative to the segment of voltage trace 405a of FIG. 4. Because the display of each voltage trace 405a-405l is synchronized and dependent on one another, the zooming and/or scrolling in one trace display window 410a-410l is simultaneously propagated to each of the other trace display windows 410a-410l. For example, changing the time period for one of pulse trains 405a-405l displayed in one of the trace display windows 410a-410l results in each of the other trace display windows 410a-410l displaying the respective voltage traces 405a-405l over the same time period.

In the example of FIG. 5, the time period of the segments of the voltage traces 405a-405l is defined between a time $t_5$ and a time $t_6$. The time t5 is later than the time t3 and the time t6 is earlier than the time t4. Consequently, the time period of the illustrated segments of voltage traces 405a-405l is less than the time period of the corresponding segments displayed in FIG. 4. As such, the trace display windows 410a-410l of FIG. 5 display a zoomed-in view of the respective voltage traces 405a-405l relative to FIG. 4. In this manner, each trace display window 410a-410l of FIG. 5 provides more specific detail of the respective voltage traces 405a-405l than those of FIG. 4. Specifically, time $t_5$ is greater than time $t_3$ and time $t_6$ is less than time $t_4$. Because each trace display window is synchronized with respect to zooming and/or scrolling, changing the time period associated with a particular trace (e.g., voltage trace 405a) results in simultaneous and synchronized changing of the time period associated with the remaining voltage traces (e.g., 405b-405l).

With continued reference to FIG. 5, the beveled scrubber bar 420 can be provided in each of the trace windows 412a-412l. In an effort to simplify the present description and more clearly illustrate features in FIG. 5, only a beveled scrubber bar 420 corresponding to display window 412a is displayed. It is appreciated, however, that a beveled scrubber bar 420 can be provided in each display window 412a-412l. The beveled scrubber bar 420 of FIG. 5 provides a viewing area 422 having a width w'. The viewing area 422 displays a portion of the voltage trace 413a-413l corresponding to the portion of the voltage trace 405a-405l displayed in trace display windows 410a-410l. Accordingly, the width w' generally corresponds to the time period of the voltage traces 405a-405l. In the example of FIG. 5, the width w' corresponds to the time period between time $t_5$ and $t_6$. Consequently, the width w' of FIG. 5 is shorter than the width w of FIG. 4.

In some examples, changing the time period associated with pulse train 405a results in providing a sixth time period that has substantially the same magnitude of the second time period; however, the sixth time period is defined between times differing than that of times $t_3$ and $t_4$. Thus, partial view modules 410a displays pulse train 405a that is "scrolled" with respect to FIG. 4. Further, similar to that as mentioned above, when the time periods of one of the pulse trains 405 displayed by the partial view modules 410 is changed, the remaining pulse trains 405 are changed in substantially the same way.

Implementations of the present disclosure provide synchronized scrolling of the segments of the voltage traces 405a-405l displayed in the trace display windows 410a-410l. For example, user input can be provided to one or more of the trace display windows 410a-410l, the user input indicating a user command for scrolling of the voltage traces 405a-405l. A scrolling command input using any one of the trace display windows 410a-410l results in an equivalent and synchronized scrolling in all of the trace display windows 410a-410l.

Figure 6:
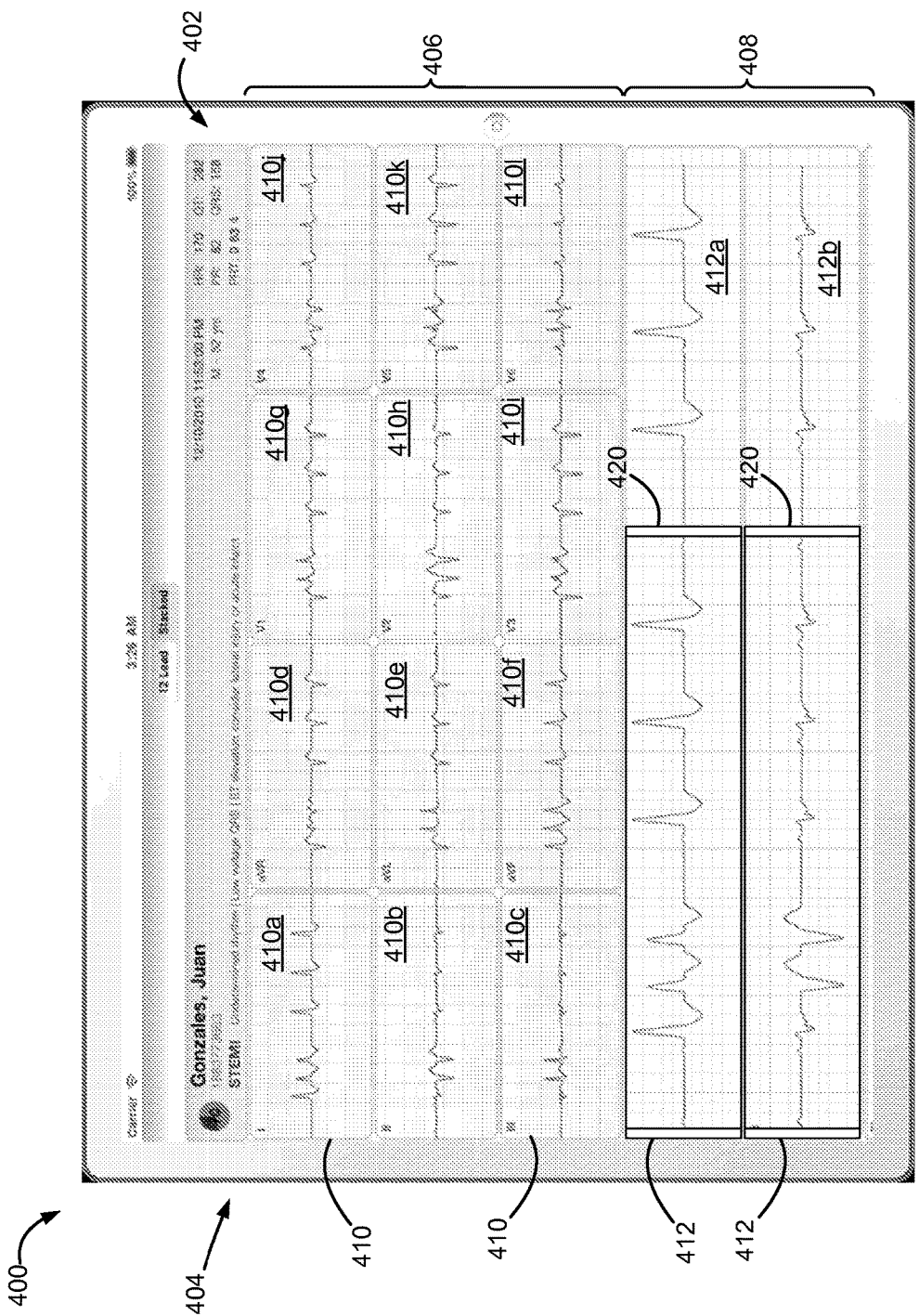

FIG. 6 depicts GUI 400 displayed in a landscape view. The landscape view of GUI 400 provides for wider trace display windows 410a-410l. In this manner, a greater amount of time (i.e., a longer segment) of the voltage traces 405a-405l can be displayed within each of the trace display windows 410a-410l, as compared to the portrait views of FIGS. 4 and 5. Similarly, more detail can be provided for the full traces 413a-413l displayed in the trace display windows 412a-412l.

Figure 7:
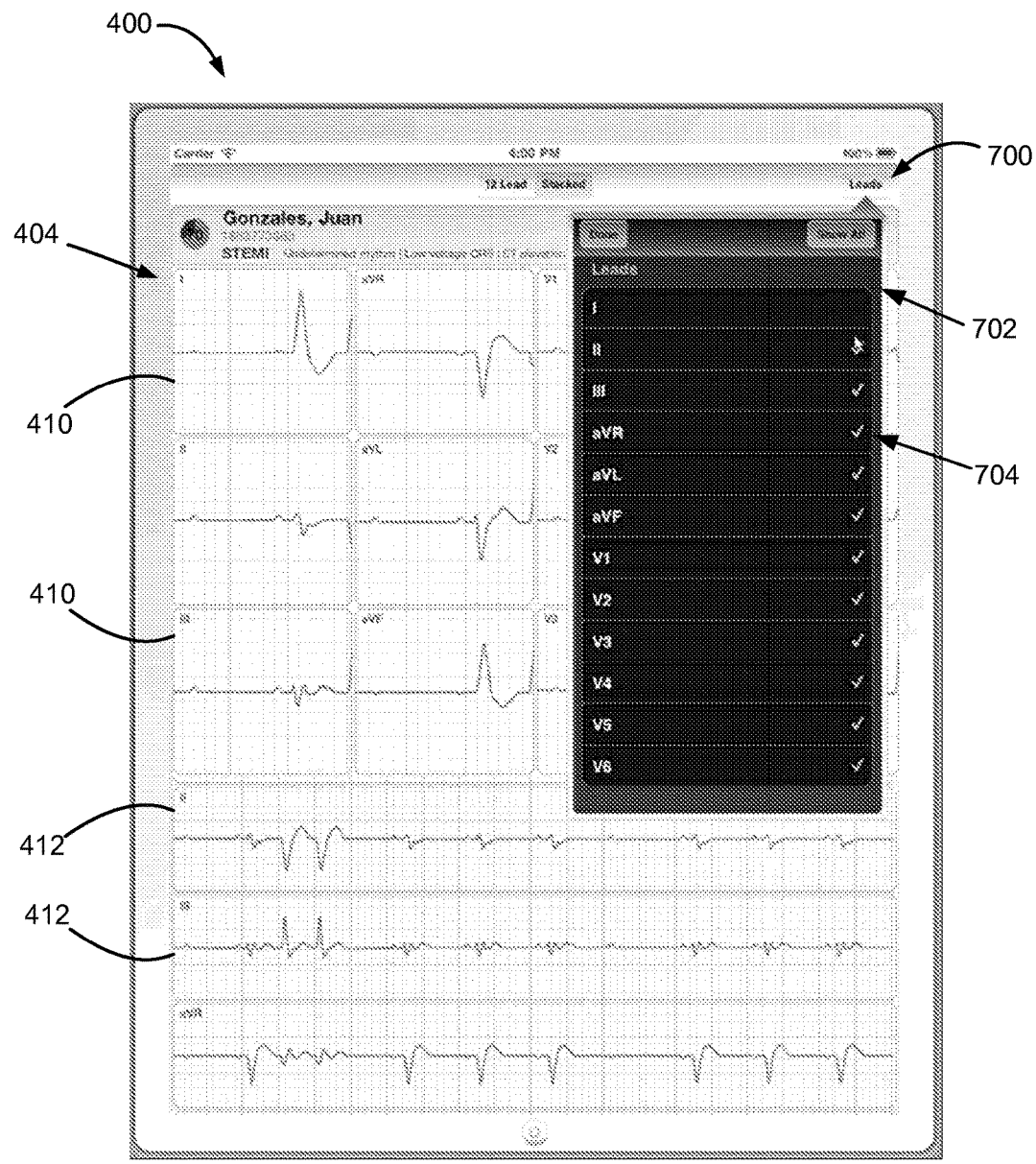

With reference to FIG. 7, user input can be provided to select a "Leads" button 700 to display a drop down menu 702. The drop down menu 702 lists the name of each of the leads (e.g., I, II, III, aVR, aVL, aVF and $V_1$-$V_6$) and an associated status identifier 704 (e.g., a checkmark). If the status identifier 704 is present, the voltage trace for the corresponding lead is to be displayed in the first display portion 406. For example, by providing user input to the status identifier 704, the check mark can be removed indicating that, upon closing the drop down menu 702 and refreshing the first display portion, the trace display window 410a and the corresponding voltage trace 405a are removed from display. In this manner, trace display windows 410a-410l can be selectively displayed in any combination. By unchecking each of the leads in the drop down menu, none of the trace display windows 410a-410l are displayed.

Figure 8:
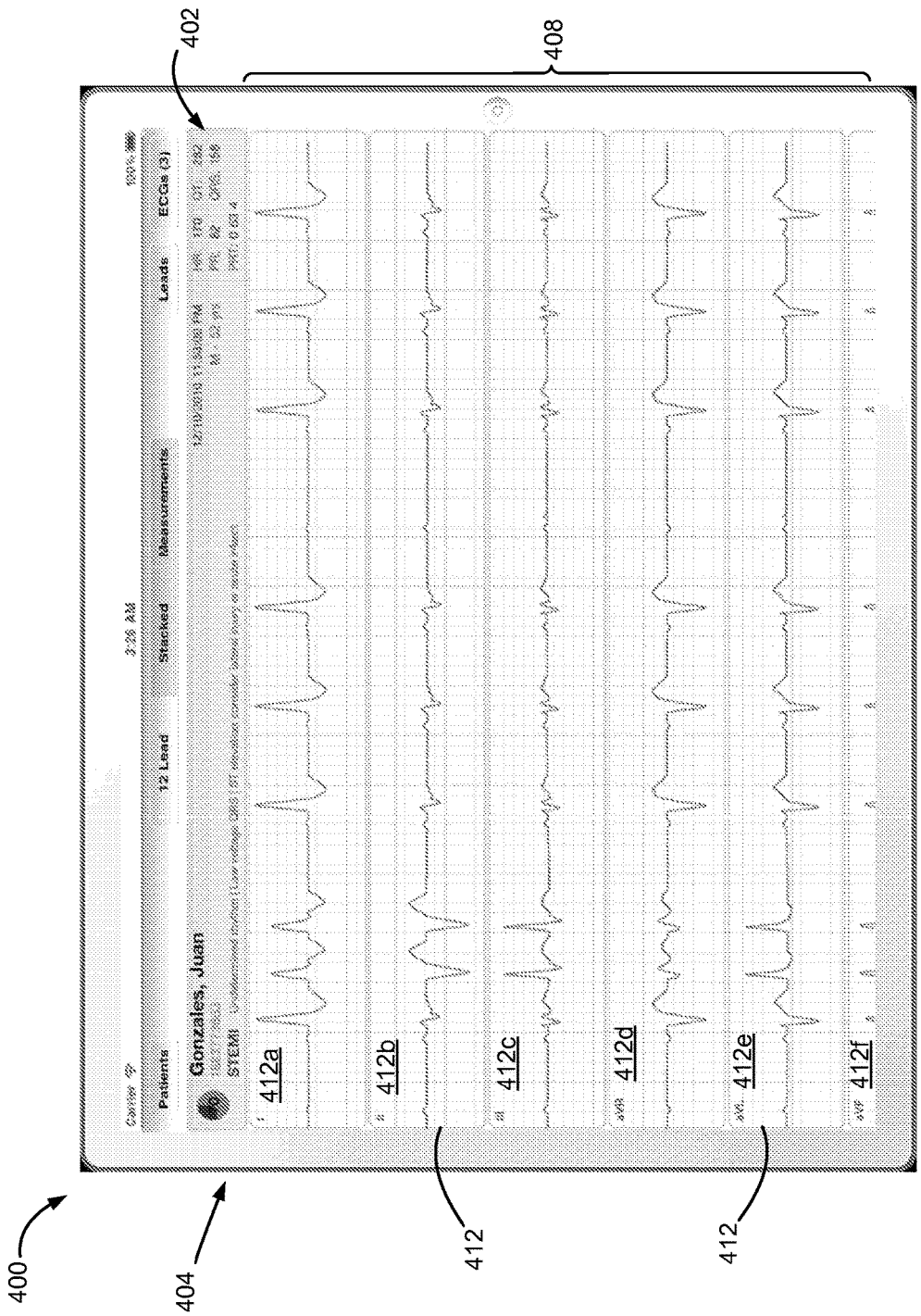

FIG. 8 depicts GUI 400 including only the second display portion 408. Specifically, GUI 400 includes selection buttons 800 and 802. When button 800 is selected (the "12 lead" button), only second display portion 408 is displayed within GUI 400. Consequently, a greater number of trace display windows 412a-412l are displayed within the second display portion 408 as compared to that shown in FIG. 4. As shown, the second display portion 408 of FIG. 8 displays full trace display windows 412a-412e and a portion of trace display window 412f. When button 802 is selected (the "stacked" button) both the first and second display portions 406 and 408 are displayed within GUI 400, as shown in FIG. 4. In some examples, GUI 400 includes only first display portion 406.

Figure 9:
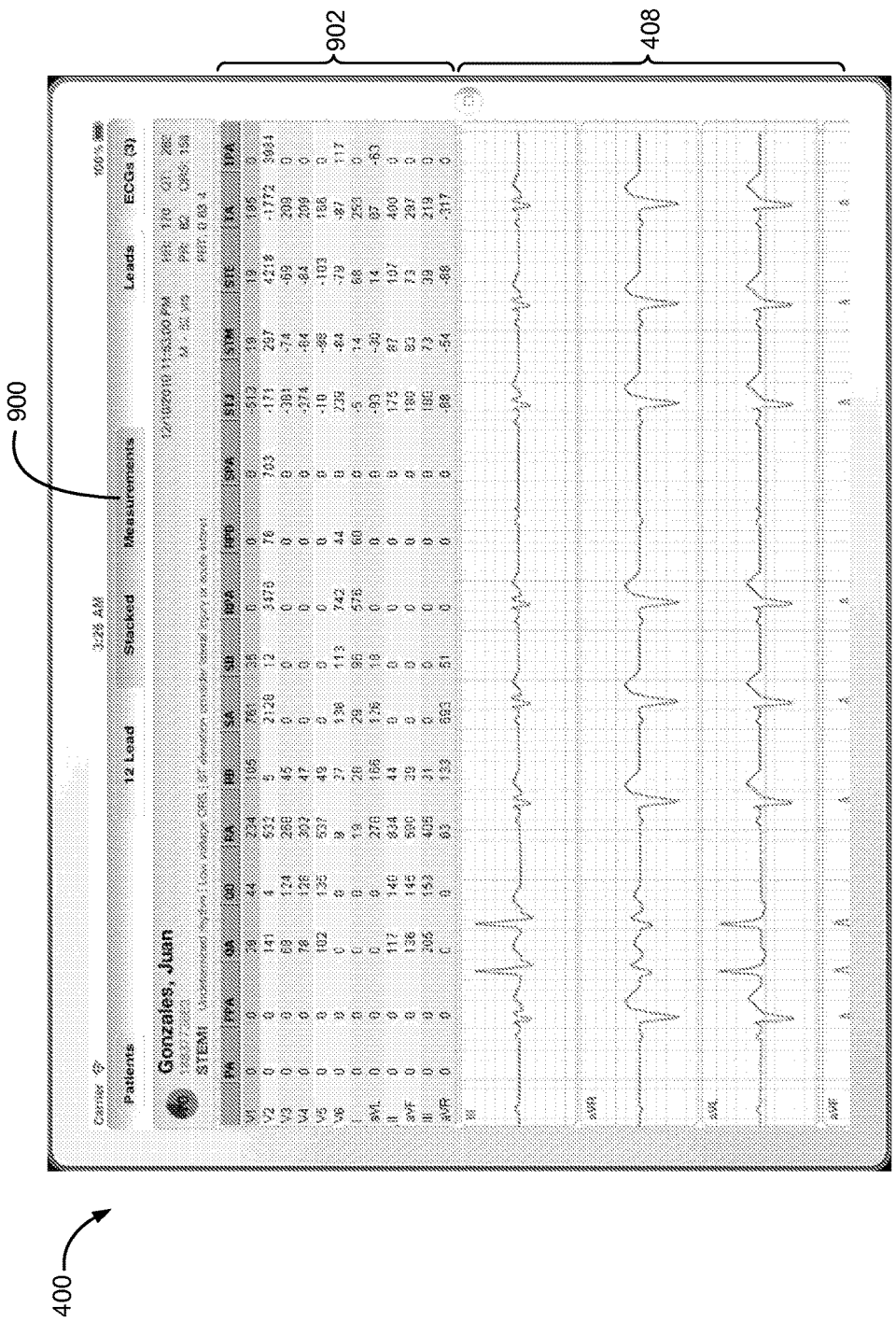

FIG. 9 depicts GUI 400 including a measurement display portion 902 and the second display portion 408. A "Measurements" button 900 is provided and can be selected by the user. In response to user input using the button 900, the display portion 902 is provided and displays the data underlying the currently displayed ECG. In this manner, the user is not only able to view a graphical representation of the data in the form of the voltage traces 405a-405l; 413a-413l, the user is also able to review the data underlying the graphical representations. In the illustrated embodiment, the data is provided in tabular form, generally as a spreadsheet. It is appreciated that the data can be presented in any number of manners. Regardless of how presented, the data presented in the display portion 902 can be scrolled to reveal columns and/or rows of data that may be hidden from view.

Figure 10:
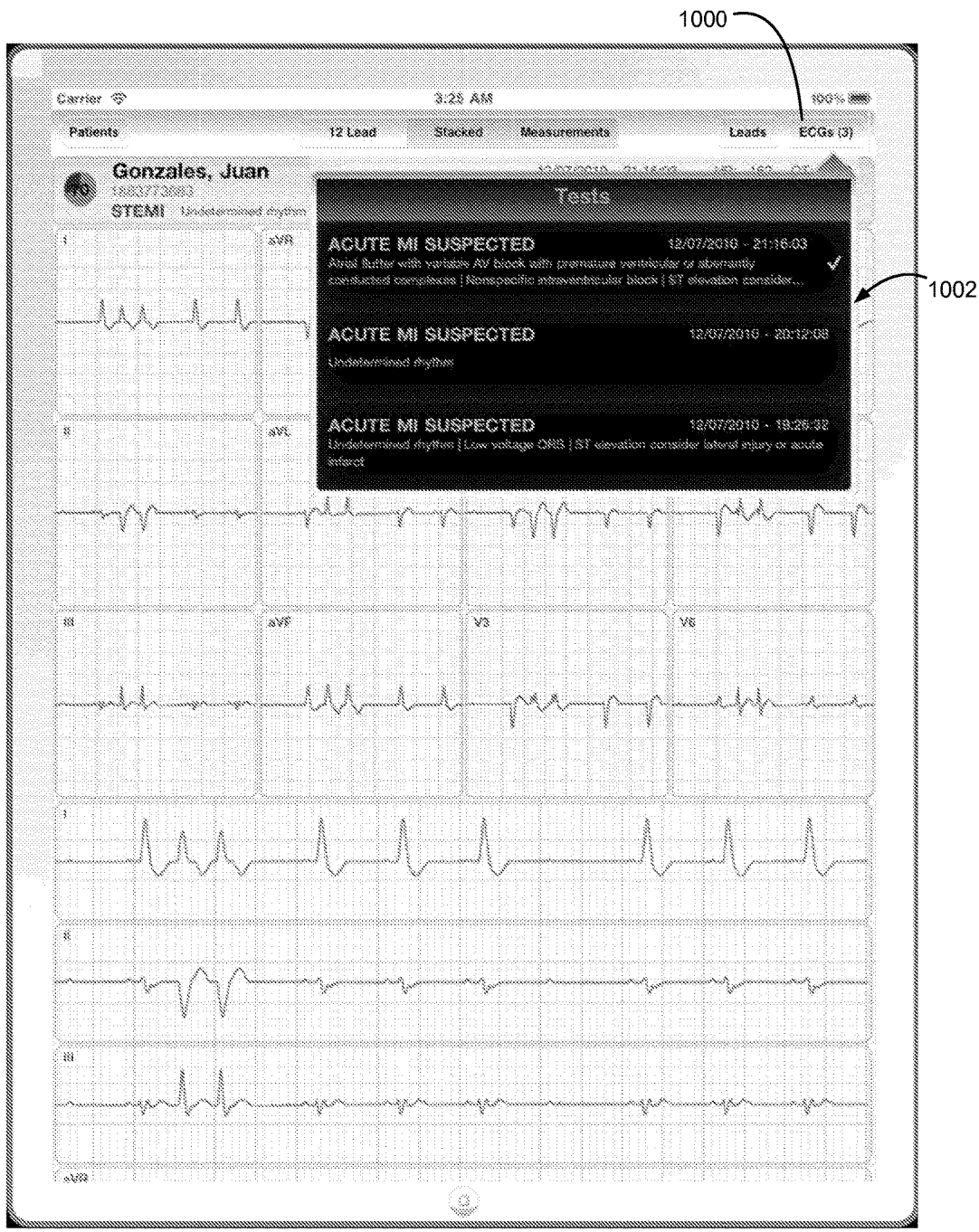

FIG. 10 depicts GUI 400 including an ECG selection menu 1002. An "ECG" button 1000 is provided and can be selected by the user. In response to user input using the button 1000, the menu 1002 is provided and displays one or more ECGs that are currently available for viewing for a particular patient. The displayed ECGs can include a title (e.g., "Acute MI Suspected"), the time and date that the ECG was performed, and a brief summary or abstract of the ECG (e.g., "Undetermined rhythm"). In the example of FIG. 10, three different ECGs can be selected for viewing for the patient "Juan Gonzales." The currently displayed ECG is indicated by a graphical indicator (e.g., a checkmark). The user can select an ECG for display from the menu 1002. For example, the user can provide tactile user input via a touch-screen to select a particular ECG. In response to the user input, the corresponding ECG data is graphically presented in the display portions 406, 408. As more ECGs are performed and the corresponding ECG data is provided to the remote device, the menu 1002 is updated.

Figure 11:
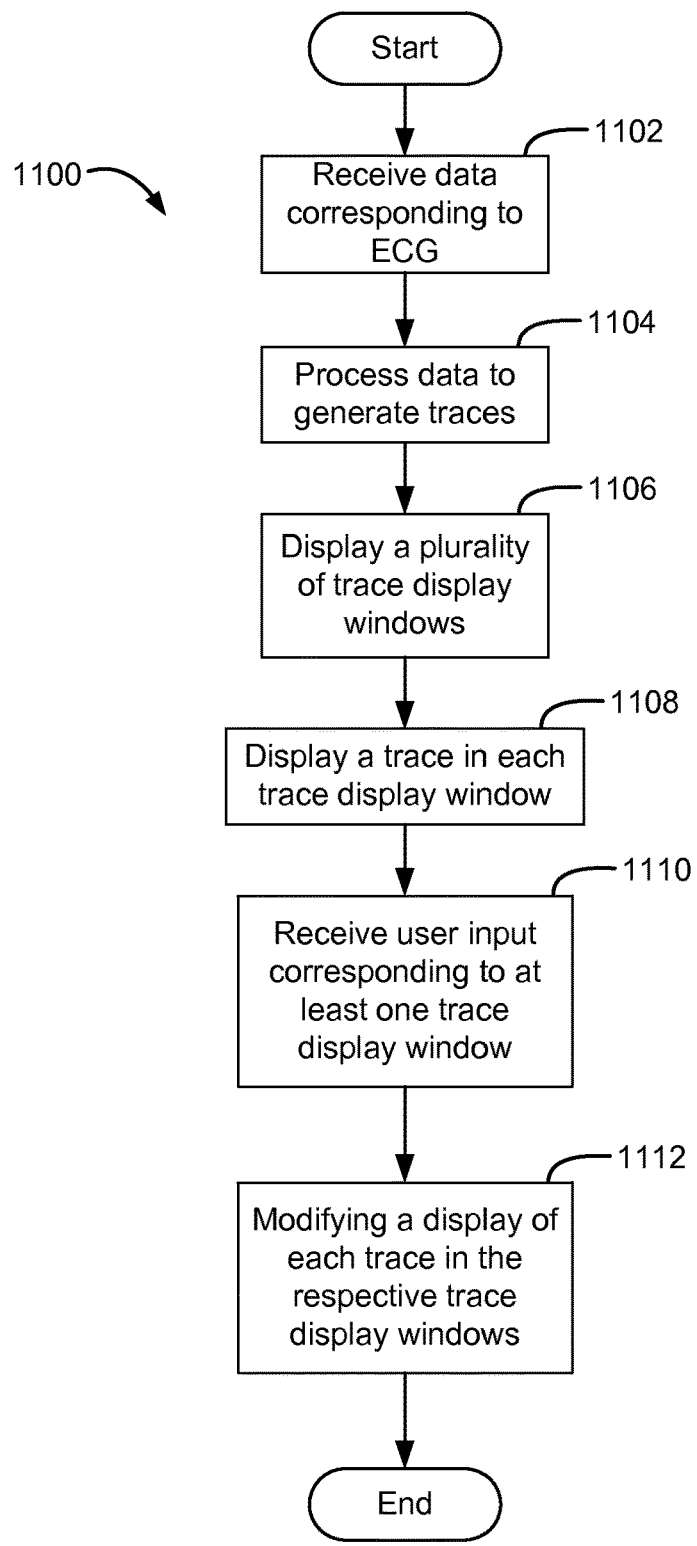
FIG. 11 is a flowchart illustrating an example process that can be executed device in accordance with implementations of the present disclosure.

FIG. 11 depicts an example process 1100 that can be executed in accordance with implementations of the present disclosure. Data corresponding to an ECG is received (1102). For example, the remote device 12 of FIG. 1 received data corresponding to an ECG from the DMS 60 of FIG. 1. The data is processed to generate a plurality of traces (1104). For example, the remote device 12 of FIG. 1 processes the data to generate the plurality of traces. A plurality of trace display windows is displayed (1106) and a trace is displayed in each trace display window (1108). For example, the remote device 12 of FIG. 1 displays the plurality of trace display windows and a respective trace in each trace display window on the display 22. User input corresponding to at least one trace window of the plurality of trace windows is received (1110). For example, the remote device 12 of FIG. 1 receives user input based on a touch-screen event (e.g., the user of the remote device 12 provides tactile user input to the display 22). A display of each trace of the plurality of traces is modified in the respective trace display windows in response to the user input (1112). For example, the remote device 12 of FIG. 1 modifies the display of each of the traces within their respective trace display windows in response to and based on the user input. For example, if the user input indicates a zoom event, each trace is simultaneously zoomed in a synchronized manner to the same degree, the degree of zoom being defined based on the user input. As another example, if the user input indicates a scroll event, each trace is simultaneously scrolled in a synchronized manner to the same degree, the degree of scroll being defined based on the user input (e.g., if one trace is scrolled forward/backward by X seconds, all traces are simultaneously scrolled forward/backward by X seconds).

Implementations of the present disclosure and all of the functional operations provided herein can be realized in digital electronic circuitry, or in computer software, firmware, or hardware, including the structures disclosed in this specification and their structural equivalents, or in combinations of one or more of them. Implementations of the present disclosure can be realized as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this disclose can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the present disclosure can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other.

While this disclosure includes some specifics, these should not be construed as limitations on the scope of the disclosure or of what may be claimed, but rather as descriptions of features of example implementations of the disclosure. Certain features that are described in this disclosure in the context of separate implementations can also be provided in combination in a single implementation. Conversely, various features that are described in the context of a single implementation can also be provided in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method for displaying an electrocardiogram (ECG) on a remote computing device, the method being executed by one or more processors and comprising:
receiving, by the remote computing device from a data management system, patient data corresponding to the ECG, the data management system comprising a synchronization services module and an adapter services module, the synchronization services module being configured to communicate with the adapter services module to selectively synchronize patient data using a synchronization rule based on variable configuration parameters, wherein the synchronized patient data is a portion of all data available for retrieval from a plurality of waveform data sources and retrieved by the adapter services module, and wherein the adapter services module being further configured to format the retrieved patient data to enable patient data synchronization independent of an operating system type of the remote computing device;
displaying a first trace of a plurality of traces in a first trace window of a plurality of trace windows, the first trace being over a first time interval, and each trace window displaying a single trace;
displaying a second trace of the plurality of traces in a second trace window over the first time interval, the first trace and the second trace being synchronized in time with and dependent on each other, at least one trace window of the plurality of trace windows comprising a graphical indicator that marks a first time portion within the first time interval;
receiving user input corresponding to the first trace window of the plurality of trace windows, the user input defining a second time interval different than the first time interval; and in response to receiving the user input, simultaneously modifying display of each of the first trace in the first trace window, and the second trace in the second trace window to be displayed over the second time interval, such that the graphical indicator marks a second time portion within the second time interval of each trace of the plurality of traces,
wherein at least one or more of the first trace, the second trace, and the plurality of traces are generated from the patient data as formatted and synchronized and not the patient data as stored by the plurality of waveform data sources.

2. The method of claim 1, wherein the user input indicates a zoom event, and modifying comprises zooming each trace within a respective trace display window.

3. The method of claim 1, wherein the user input indicates a scroll event, and modifying comprises scrolling each trace within a respective trace display window.

4. The method of claim 1, wherein modifying the display of each trace comprises simultaneous and time synchronized modification of each trace.

5. The method of claim 1, further comprising:
processing the patient data to generate a plurality of full traces;
displaying a plurality of full trace display windows; and
displaying each full trace of the plurality of full traces in a full trace window of the plurality of full trace windows.

6. The method of claim 5, wherein the plurality of full traces displayed in the plurality of full trace display windows remain unmodified in response to the user input.

7. A non-transitory computer-readable storage device coupled to one or more processors and having instructions stored thereon which, when executed by the one or more processors, cause the one or more processors to perform operations comprising:
receiving, by a remote computing device from a data management system, patient data corresponding to an electrocardiogram (ECG), the data management system comprising a synchronization services module and an adapter services module, the synchronization services module being configured to communicate with the adapter services module to selectively synchronize patient data using a synchronization rule based on variable configuration parameters, wherein the synchronized patient data is a portion of all data available for retrieval from a plurality of waveform data sources and retrieved by the adapter services module, and wherein the adapter services module being further configured to format the retrieved patient data to enable patient data synchronization independent of an operating system type of the remote computing device;
displaying a first trace of a plurality of traces in a first trace window of a plurality of trace windows, the first trace being over a first time interval, and each trace window displaying a single trace;
displaying a second trace of the plurality of traces in a second trace window over the first time interval, the first trace and the second trace being synchronized in time with and dependent on each other, at least one trace window of the plurality of trace windows comprising a graphical indicator that marks a first time portion within the first time interval;
receiving user input corresponding to the first trace window of the plurality of trace windows, the user input defining a second time interval different than the first time interval; and
in response to receiving the user input, simultaneously modifying display of each of the first trace in the first trace window, and the second trace in the second trace window to be displayed over the second time interval, such that the graphical indicator marks a second time portion within the second time interval of each trace of the plurality of traces,
wherein at least one or more of the first trace, the second trace, and the plurality of traces are generated from the patient data as for matted and synchronized and not the patient data as stored by the plurality of waveform data sources.

8. The computer-readable storage device of claim 7, wherein the user input indicates a zoom event, and modifying comprises zooming each trace within a respective trace display window.

9. The computer-readable storage device of claim 7, wherein the user input indicates a scroll event, and modifying comprises scrolling each trace within a respective trace display window.

10. The computer-readable storage device of claim 7, wherein modifying the display of each trace comprises simultaneous and time synchronized modification of each trace.

11. The computer-readable storage device of claim 7, wherein operations further comprise:
processing the patient data to generate a plurality of full traces;

displaying a plurality of full trace display windows; and displaying each full trace of the plurality of full traces in a full trace window of the plurality of full trace windows.

12. The computer-readable storage device of claim 11, wherein the plurality of full traces displayed in the plurality of full trace display windows remain unmodified in response to the user input.

13. A system, comprising:

a remote computing device; and a computer-readable storage device coupled to the remote computing device and having instructions stored thereon which, when executed by the remote computing device, cause the computing device to perform operations comprising:

receiving, by the remote computing device from a data management system, patient data corresponding to an electrocardiogram (ECG), the data management system comprising a synchronization services module and an adapter services module, the synchronization services module being configured to communicate with the adapter services module to selectively synchronize patient data using a synchronization rule based on variable configuration parameters, wherein the synchronized patient data is a portion of all data available for retrieval from a plurality of waveform data sources and retrieved by the adapter services module, and wherein the adapter services module being further configured to format the retrieved patient data to enable patient data synchronization independent of an operating system type of the remote computing device;

displaying a first trace of a plurality of traces in a first trace window of a plurality of trace windows, the first trace being over a first time interval, and each trace window displaying a single trace;

displaying a second trace of the plurality of traces in a second trace window over the first time interval, the first trace and the second trace being synchronized in time with and dependent on each other, at least one trace window of the plurality of trace windows comprising a graphical indicator that marks a first time portion within the first time interval;

receiving user input corresponding to the first trace window of the plurality of trace windows, the user input defining a second time interval different than the first time interval; and in response to receiving the user input, simultaneously modifying display of each of the first trace in the first trace window, and the second trace in the second trace window to be displayed over the second time interval, such that the graphical indicator marks a second time portion within the second time interval of each trace of the plurality of traces, wherein at least one or more of the first trace, the second trace, and the plurality of traces are generated from the patient data as formatted and synchronized and not the patient data as stored by the plurality of waveform data sources.

14. The system of claim 13, wherein the user input indicates a zoom event, and modifying comprises zooming each trace within a respective trace display window.

15. The system of claim 13, wherein the user input indicates a scroll event, and modifying comprises scrolling each trace within a respective trace display window.

16. The system of claim 13, wherein modifying the display of each trace comprises simultaneous and time synchronized modification of each trace.

17. The system of claim 13, wherein operations further comprise:

processing the patient data to generate a plurality of full traces;

displaying a plurality of full trace display windows; and displaying each full trace of the plurality of full traces in a full trace window of the plurality of full trace windows.

18. The system of claim 17, wherein the plurality of full traces displayed in the plurality of full trace display windows remain unmodified in response to the user input.

* * * * *